United States Patent [19]

Finch, Jr.

[11] Patent Number: 5,078,781
[45] Date of Patent: Jan. 7, 1992

[54] BIPYRIDILIUM HERBICIDAL COMPOSITIONS

[75] Inventor: Charles W. Finch, Jr., El Sobrante, Calif.

[73] Assignee: Imperial Chemical Industries PLC, London, United Kingdom

[21] Appl. No.: 374,705

[22] Filed: Jun. 30, 1989

[51] Int. Cl.$^5$ .................... A01N 43/40; A01N 47/30
[52] U.S. Cl. ........................... 71/94; 71/120; 71/DIG. 1
[58] Field of Search ............... 71/94, DIG. 1, 120, 71/94

[56] References Cited

FOREIGN PATENT DOCUMENTS

| | | |
|---|---|---|
| 446410 | 3/1971 | Australia . |
| 1058411 | 7/1979 | Canada . |
| 253682 | 1/1988 | European Pat. Off. . |
| 276911 | 8/1988 | European Pat. Off. . |
| 356812 | 3/1990 | European Pat. Off. . |
| 3247050 | 6/1984 | Fed. Rep. of Germany . |
| 58-110506 | 7/1983 | Japan . |
| 59-70602 | 4/1984 | Japan . |
| 60-163801 | 8/1985 | Japan . |
| 8063530 | 12/1988 | Japan . |
| 966852 | 8/1964 | United Kingdom . |
| 1088981 | 10/1967 | United Kingdom . |
| 1170927 | 11/1969 | United Kingdom . |
| 1453443 | 10/1974 | United Kingdom . |
| 1421133 | 1/1976 | United Kingdom . |
| 1502259 | 3/1978 | United Kingdom . |

OTHER PUBLICATIONS

Headford, Pesticide Science, vol. 1, pp. 41–42 (1970).
Herbicides in the Americas–Gramocil Information Bulletin, Imperial Chemical Industries PLC (1984).
Surefire Herbicide Application Guide and two Supplemental Phamplets (ICI Americas Inc.).

Primary Examiner—Richard L. Raymond
Assistant Examiner—B. Bembenick
Attorney, Agent, or Firm—Joel G. Ackerman

[57] ABSTRACT

Liquid compositions comprising:
(a) a bipyridilium herbicide;
(b) a photosynthesis-inhibiting herbicide;
(c) a normally water-insoluble oil in which the photosynthesis-inhibiting herbicide (b) is soluble;
(d) water; and
(e) a surfactant selected from:
  (i) a polyalkyl glucoside;
  (ii) a polyoxypropylene-polyoxyethylene block copolymer;
  (iii) an alkyl trimethyl ammonium salt; and
  (iv) a mixture of polyvinyl alcohol with a surfactant having an HLB value from about 13 to about 20.

11 Claims, No Drawings

BIPYRIDILIUM HERBICIDAL COMPOSITIONS

BACKGROUND AND PRIOR ART

This invention concerns improved herbicidal compositions containing a bipyridilium herbicide and at least one herbicide which has the ability to inhibit photosynthesis.

Bipyridilium herbicides are a well known class of herbicides having the general formulas

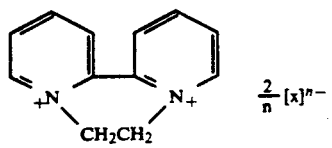

and

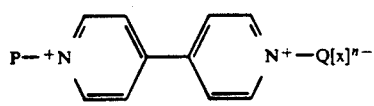

in which P and Q, which may be the same or different, are $C_1$-$C_4$ alkyl which may be substituted by hydroxyl, halogen, carboxyl, alkoxy, alkylcarbonyl, alkoxycarbonyl, carbamoyl or N-substituted carbamoyl; X is an anion, preferably a halide, and n is an integer from 1 to 4. The two most prominent members are paraquat (1,1'-dimethyl-4,4'- bipyridilium ion and/or its salts) and diquat (1,1'-ethylene-2,2'- bipyridilium ion and/or its salts). Other bipyridilium herbicides are mentioned, for example, in Canadian patent 1,058,411. Bipyridilium herbicides, particularly paraquat, are non-selective contact herbicides which kill those plant tissues which carry out photosynthesis. As is well known, paraquat, for instance, is reduced in the presence of free electrons produced during the photosynthesis process to paraquat free radicals. In the presence of oxygen, these free radicals are quickly re-oxidized to paraquat, producing hydrogen peroxide and/or a so-called "superoxide", which cause rapid desiccation of plant tissues.

It is well known that paraquat is used most effectively in conditions of dim light, for instance on cloudy or overcast days, or towards evening. Under such conditions, photosynthesis proceeds more slowly, and the paraquat has an opportunity to translocate more through the plant, giving a more complete kill when it becomes activated. When paraquat is applied in bright sunny conditions when photosynthetic rate is high, paraquat reduction together with generation of toxic oxides is rapid, often so rapid that the paraquat effect remains localized near the point of its application. Application of paraquat under bright sunlight, therefore, can produce a quick effect, but significant re-growth can occur.

However, it is often impractical or inconvenient to apply paraquat under only those low light conditions which produce optimum activity. It has been found therefore, for instance by Headford, Pesticide Science, Vol. 1, pp. 41-42 (1970) that similar optimum effects can be obtained by combining paraquat with another compound, particularly another herbicide, which has the ability to inhibit photosynthesis. Headford found that a combination of paraquat and bromacil, at a 2:1 weight ratio, sprayed in full sunlight, gave effects similar to those from paraquat alone sprayed at 5:00 P.M. It also has been recommended to tank mix paraquat with a number of other herbicides, including at least one (linuron) which coincidentally is a photosynthesis inhibitor. In using tank mixes of paraquat with photosynthesis inhibiting herbicides, the best activity would be expected from the most water-soluble photosynthesis inhibitor, which would allow the paraquat to best translocate for a more complete kill. However, the most active photosynthesis-inhibiting herbicides are typically water insoluble.

In addition, simple tank mixes of paraquat with, for instance, wettable powder formulations of other herbicides, do not produce consistent effects in terms of optimum translocation and effect of paraquat.

As an improvement over tank mixes of paraquat and photosynthesis inhibiting herbicides, a formulation in the form of a stabilized suspension concentrate containing paraquat and diuron, in a 2:1 weight ratio, has been sold under the trademark Surefire. However, as with previously suggested combinations, the photosynthesis-inhibiting herbicide (in this case, diuron) is used in one-half the amount of the paraquat in order to provide the desired optimum paraquat translocation and herbicidal effect. It would be advantageous to obtain at least a similar effect with the use of much lower quantities of the photosynthesis inhibitor.

SUMMARY OF THE INVENTION

In one aspect this invention comprises a liquid herbicidal composition comprising:
 (a) a herbicidally effective amount of a bipyridilium herbicide;
 (b) a photosynthesis-inhibiting herbicide;
 (c) a normally water-insoluble oil in which the photosynthesis-inhibiting herbicide (b) is soluble;
 (d) water; and
 (e) a surfactant selected from:
  (i) a polyalkyl glucoside;
  (ii) a polyoxypropylene-polyoxyethylene block copolymer;
  (iii) an alkyl trimethyl or dialkyl dimethyl ammonium salt; and
  (iv) a mixture of polyvinyl alcohol with a surfactant having an HLB value from about 13 to about 20.

In another aspect, this invention comprises a process for producing a composition of the type just mentioned which comprises contacting a solution of the photosynthesis-inhibiting herbicide in the water-insoluble oil with an aqueous solution of the bipyridilium herbicide containing the surfactant.

The invention also comprises a liquid composition containing a photosynthesis-inhibiting herbicide which can be tank mixed with an aqueous solution of a bipyridilium herbicide such as paraquat to produce the first-mentioned liquid herbicidal composition, which contains a photosynthesis-inhibiting herbicide, a normally water-insoluble oil in which the photosynthesis-inhibiting herbicide is soluble and an alkyl trimethyl or dialkyl dimethyl ammonium salt.

DETAILED DESCRIPTION OF THE INVENTION

The compositions of this invention have at least two herbicides: a bipyridilium herbicide, and a second herbicide which has the property of inhibiting photosynthesis. In addition, as will be mentioned below, such compositions may also contain other herbicides.

The bipyridilium herbicide may be paraquat, a herbicide which has been sold in many countries for a large variety of uses, or diquat.

The second herbicide is one which has the property of inhibiting photosynthesis. Solubility in water is desirable for a photosynthesis inhibiting herbicide used together with paraquat, since such solubility would enable the herbicide to penetrate quickly and/or be more readily translocatable in the plant. However, the more active herbicides having this property tend to be insoluble in water. The compositions and process of the present invention have as one feature the ability to utilize the more active but relatively water-insoluble photosynthesis-inhibiting herbicides. Examples of such herbicides which can be used in combination with paraquat or diquat or other bipyridilium herbicides in the compositions of the present invention include: triazines, such as atrazine, ametryne, desmetryne, and prometryne; phenyl ureas such as diuron, neburon, linuron, chloroxuron and monuron; uracils such as bromacil, lenacil, and terbacil; aryl alkanamides such as karsil, napropamide and propanil; triazineones such as metribuzin; carbamates such as phenmedipham; anilides such as cypromide and chloranocryl and benzonitriles such as ioxynil.

Other photosynthesis-inhibiting herbicides can be used, as long as they do not dissociate into anions which could react with the paraquat or diquat cation.

In addition to the bipyridilium herbicide and the photosynthesis-inhibiting herbicide, compositions according to this invention may also contain one or more additional herbicides which may be used in combination with the bipyridilium herbicide to achieve additional control. Such herbicides include, for instance, fluazifop-P-butyl, alachor, metolachlor, dicamba, bifenox, and pendimethalin.

The oils, or organic liquids, suitable for use in the compositions of this invention are those organic liquids which are essentially water-insoluble but in which the photosynthesis-inhibiting herbicide is soluble. Suitable oils for use in this invention include water-insoluble alcohols such as tetrahydrofurfuryl alcohol, n-pentanol and n-hexanol; aromatic hydrocarbons such as toluene, xylenes and naphthalenic solvents; halohydrocarbons such as monochlorotoluene; ketones such as mesityl oxide, cyclohexanone, 2-heptanone, isophorone and acetophenone; esters such as t-butyl phosphate and isoamyl acetate; nitrogen-containing compounds such as pyridine, nitrobenzene and dimethylformamide; and phenols such as phenol and nonylphenols.

The surfactant in this composition plays an essential role. When the solution of photosynthesis-inhibiting herbicide in the oil phase is contacted with an aqueous solution of the bipyridilium herbicide in the presence of the surfactant, the inner hydrophobic portion of the surfactant micelle dissolves the mixture of photosynthesis-inhibiting herbicide and oil. The resulting composition may be termed a "soluble liquid" since the oil and the photosynthesis-inhibiting herbicide contained in it are now "soluble" in water. Four different types of surfactants have been found suitable for use in these compositions. They are:

(a) polyalkyl glucosides;
(b) polyoxypropylene-polyoxyethylene block co-polymers;
(c) alkyl trimethyl and dialkyl dimethyl quaternary ammonium salts; and
(d) mixtures of polyvinyl alcohol with surfactants having an HLB value of between about 13 and about 20.

Polyalkyl glucosides have the general formula

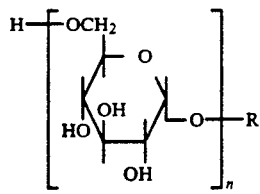

in which R is a $C_4$–$C_{22}$ aliphatic group, preferably a $C_8$–$C_{16}$ aliphatic group, and n has an average value of from about 1 to about 20, preferably from about 1 to about 5, and most preferably from about 1.4 to about 2.4. One example of such a surfactant is AL-2233, in which R is a mixture of $C_8$ and $C_{10}$ groups and n has an average value of about 1.5–2.0. It is produced by the reaction of a mixture of octyl and decyl alcohols with glucose under controlled polymerization conditions and is sold as an aqueous solution by ICI Americas Inc.

Polyoxyethylene-polyoxypropylene block copolymers have the general formula:

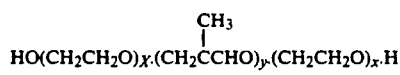

and have molecular weights averaging from about 1,000 to about 1,500. They are generally produced by controlled addition of propylene oxide to propylene glycol, followed by addition of ethylene oxide. Some examples of such surfactants are Pluronic L35, L44 and L64 sold by BASF Corporation.

Alkyl trimethyl ammonium and dialkyl dimethyl ammonium salts have the general formulas, respectively:

in which R and R' represent an alkyl group or mixture of alkyl groups having from about 8 to about 18 carbon atoms and X is an anion, usually a halide. One example of such a surfactant is Arquad C-50 (trimethyl coco ammonium chloride) which is sold by Akzo Chemie America. Other similar surfactants also sold by Akzo Chemie America have as the alkyl group dodecyl or hexadecyl.

The fourth type of surfactant is a mixture of polyvinyl alcohol with a surfactant having an HLB value of from about 13 to about 20. Surfactants of this type include, for instance, ethoxylated sorbitan esters such as Tween 20, 40, 60 and 80, ethoxylated castor oil surfactants such as Etocas 100, Alcasurf C0200, Chemmax C0-200/50 and Pegosperse C0200; polyoxyethylene esterates such as Myrj 53, Brig 700 and Kessco EG esters; and ethoxylated alkylphenols, such as those sold under the trademark Igepal by GAF Corporation. Such alkylphenols have the general formula

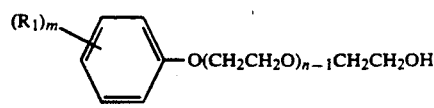

in which $R_1$ is an alkyl group having from 8 to 18 carbon atoms, m is 1 or 2 and n is from about 30 to about 150. Members of this series include Igepal surfactants CA-887, CA-890, CA-897, CO-850, CO-880 and other higher molecular weight members of the CO series, and DM-970.

The polyvinyl alcohol component of this type of surfactant may be any suitable commercial form of polyvinyl alcohol including those sold under the trademark Vinol by Air Products Co. such as Vinol 205. In general, the polyvinyl alcohol will be employed in a weight ratio of from about 0.5:1 to about 3:1 with respect to the surfactant having an HLB value of 13-20.

Compositions according to this invention will generally contain the above components in the following amounts.

Bipyridilium herbicide: from about 5 to about 30 weight percent, preferably from about 18 to about 24 weight percent;
  photosynthesis-inhibiting herbicide: from about 1 to about 12 weight percent, preferably from about 1 to 5 weight percent;
  water-insoluble oil: from about 5 to about 10 weight percent, preferably from about 7 to about 10 weight percent;
  surfactant: from about 5 to about 40 weight percent, preferably from about 8 to about 20 weight percent, most preferably from about 8 to about 12 weight percent; and
  water: the remainder.

In general, compositions according to this invention will contain the bipyridilium herbicide and the photosynthesis-inhibiting herbicide in a weight ratio, respectively, of from about 4:1 to about 25:1, preferably between about 8:1 and about 15:1. The compositions may also contain from about 6 to about 24, preferably from about 6 to about 12 weight percent of one or more additional herbicides. A preferred combination of other herbicides with a bipyridilium herbicide is a composition containing paraquat and fluazifop-P-butyl, in a weight ratio of from about 1:8 to about 2:1, respectively.

Compositions according to this invention may also contain additional ingredients, such as dispersants or freeze point depressants, which may be used to impact desirable properties but which do not adversely affect herbicidal performance.

Compositions of this invention are prepared by mixing appropriate quantities of an aqueous solution of the bipyridilium herbicide with an oil solution of the photosynthesis-inhibiting herbicide, and contacting with a surfactant as described above. The surfactant may be contained in the aqueous solution of bipyridilium herbicide before the two solutions are mixed, or may be added simultaneously with, or subsequent to, the mixing of the two solutions. The mixing is preferably mild, but greater agitation does not adversely affect the product.

For instance, for preparation of formulations containing paraquat and diuron, the oil solution of diuron and aqueous solution of paraquat are prepared separately. For the oil solution, the water-insoluble oil, for instance a mixture of mesityl oxide and Aromatic 200 are mixed with Arquad 2C-75, which in this embodiment is used as a dispersant rather than a surfactant. Then an appropriate amount of diuron is added and the mixture is heated to 50° C. to dissolve the diuron.

The aqueous solution of paraquat is prepared by addition of Vinol 205 directly to an aqueous paraquat concentrate containing 33.5 weight/weight as paraquat dichloride. The mixture is heated to 90° C. to dissolve the Vinol 205. Then the surfactant, having an HLB value between 13 and about 20, is added to complete the water phase, together with additional water if necessary and propylene glycol to prevent freezing. Subsequently, the oil solution is dispersed into the aqueous paraquat solution with mild mixing at 20°-25° C. to produce the compositions of this invention.

For use under field application conditions, the compositions are diluted with water to an appropriate concentration for spraying. The compositions of this invention, being "soluble liquids", form diluted compositions which range from semi-transparent with a particle size of 0.1-0.05 millimicrons, to clear with a particle size of less than 0.05 millimicrons. For use in no-till agriculture, for instance, it is possible to spray the compositions of this invention on the plants to be killed during one day, and have sufficient kill to be able to plant a crop on the next.

The following are representative examples of preparation of compositions according to this invention.

EXAMPLE 1

A composition containing 2.0 lbs./gallon paraquat and 0.2 lb./gallon diuron was prepared as follows: 9.7 grams (g) of mesityl oxide, 0.8 g of Aromatic 200 solvent and 7.2 g of Arquad 2C-75 dispersant were mixed in a vessel. Then, 2.2 g of diuron technical grade (95% by weight) was added, and the mixture heated to 50° C. to dissolve the diuron.

The aqueous solution was prepared by adding 2.0 g Vinol 205 to 21.9 g of a 33.5 weight percent solution of paraquat in water. The mixture was heated to 90° C. to properly dissolve the polyvinyl alcohol. Then, there was added 3.0 g of Tween 40 polyoxyethylene sorbitan ester, 2.5 g propylene glycol and 50.7 g water.

The oil solution was dispersed into the aqueous solution with mild mixing at 20°-25° C. to produce 100 g of composition.

EXAMPLE 2

Similarly to Example 1, there was prepared a composition containing 2.0 lbs./gallon paraquat and 0.08 lb./gallon diuron. It had the overall composition:

| Ingredient | Weight Percent |
| --- | --- |
| paraquat | 21.9 |
| diuron | 0.9 |
| AL2233 surfactant | 12.0 |
| Arquad 2C-75 | 5.0 |
| cyclohexanone | 2.6 |
| water | 57.6 |

EXAMPLE 3

Similarly to Example 1, there was prepared a composition containing 1.5 lb./gallon paraquat, 0.07 lb./gallon linuron and 0.24 lb./gallon fluazifop-P-butyl. This composition is represented as follows:

| Ingredient | Weight Percent |
| --- | --- |
| paraquat | 16.4 |
| linuron | 0.9 |
| fluazifop-P-butyl | 3.6 |
| AL2233 surfactant | 18.0 |
| Igepal CO630 surfactant | 10.0 |
| Arquad 2C-75 | 2.4 |
| cyclohexanone | 1.9 |

-continued

| Ingredient | Weight Percent |
|---|---|
| water | 46.8 |

EXAMPLE 4

This example represents the preparation of a concentrated emulsion of a photosynthesis-inhibiting herbicide which can be tank mixed with an aqueous solution of paraquat to produce the compositions according to this invention in the field.

Similarly to Example 1 for preparation of the oil phase, there was obtained a composition containing:

| Ingredient | Weight Percent |
|---|---|
| metribuzin | 5.8 |
| tetrahydrofurfuryl alcohol | 23.3 |
| Arquad 16/50 surfactant | 29.5 |
| Arquad 2C-75 dispersant | 41.4 |

This composition contained 0.5 lb./gallon metribuzin.

EXAMPLE 5

Similarly to Example 4, there was obtained a composition as follows:

| Ingredient | Weight Percent |
|---|---|
| diuron | 5.8 |
| Arquad 16/50 surfactant | 29.5 |
| Arquad 2C-75 dispersant | 41.4 |
| cyclohexanone | 23.3 |

This composition contained 0.5 lb./gallon diuron.

HERBICIDAL ACTIVITY

Compositions were prepared containing paraquat, diuron, a surfactant, and in some cases, fluazifop-P-butyl, by mixing appropriate amounts of the following materials: paraquat-an aqueous solution containing 1.5 pounds/gallon paraquat; diuron-an emulsifiable concentrate corresponding to the formula of Example 5 and containing 0.5 pounds/gallon diuron; and fluazifop-P-butylan emulsifiable concentrate containing 1.0 pound fluazifopbutyl/gallon. Compositions containing fluazifop-P-butyl corresponded to the composition of Example 3 with linuron replaced by diuron. Minor amounts of Ortho X-77, a crop oil, were included to lower the surface tension in some tests. The compositions were diluted with water and sprayed on test plots containing various annual grasses and broadleaf weeds, including *Echinochloa crusqalli, Dioitaria sanquinalis, Ipomoea hederacea, Seturia viridis* and *Abutilon theophrasti* so as to provide application rates of the individual components as indicated below in Table 1.

Trials were carried out at three locations. The following Table 1 shows the data obtained in these evaluations, rated various days after treatment as indicated.

Also included in these evaluations, for comparison, was a composition sold under the trademark Surefire, which contained a 2:1 weight ratio of paraquat:diuron and was sprayed so as to apply these two herbicides at rates of 0.35 and 0.18 pounds/acre, respectively.

TABLE 1

| Application rate lb./acre | | | % control | | | | | |
|---|---|---|---|---|---|---|---|---|
| | | | TEST 1 | | TEST 2 | | TEST 3 | |
| P | D | F | GR | BL | GR | BL | GR | BL |
| 0.35 | 0.088 | — | 96 | 90 | 76 | 67 | 92 | 73 |
| 0.35 | 0.044 | — | 89 | 85 | 77 | 66 | 89 | 72 |
| 0.35 | 0.029 | — | 86 | 82 | 80 | 70 | 2 | 67 |
| 0.35 | 0.014 | — | 68 | 81 | 77 | 67 | 77 | 77 |
| 0.35 | 0.088 | 0.05 | 97 | 87 | 88 | 71 | 96 | 70 |
| 0.35 | 0.044 | 0.05 | 93 | 85 | 89 | 66 | 94 | 81 |
| 0.35 | 0.029 | 0.05 | 95 | 86 | 87 | 61 | 91 | 72 |
| 0.35 | 0.014 | 0.05 | 89 | 84 | 90 | 61 | 91 | 75 |
| 0.35 | 0.088 | 0.10 | 100 | 91 | 90 | 72 | 96 | 79 |
| 0.35 | 0.044 | 0.10 | 99 | 93 | 91 | 66 | 96 | 80 |
| 0.35 | 0.029 | 0.10 | 97 | 84 | 92 | 70 | 97 | 74 |
| 0.35 | 0.014 | 0.10 | 92 | 86 | 92 | 69 | 97 | 74 |
| *0.35 | 0.18 | — | 84 | 82 | 82 | 68 | 83 | 64 |
| 0.35 | — | — | 54 | 76 | 81 | 68 | 61 | 51 |
| 0.35** | — | — | 39 | 79 | 78 | 69 | 73 | 76 |
| — | — | 0.1 | 82 | 0 | 31 | 0 | 67 | 0 |
| — | — | 0.1** | 84 | 8 | 32 | 0 | 92 | 5 |

KEY:
P = paraquat
D = diuron
F = fluazifop-P-butyl
GR = grassy weeds
BL = broadleaf weeks
*Surefire
**with Ortho X-77
Test 1 was conducted at Goldsboro, North Carolina and was rated 24 days after treatment.
Test 2 was conducted at Visalia, California and was rated 8 days after treatment.
Test 3 was conducted at Leland, Mississippi and was rated 21 days after treatment.

As can be seen from the above Table 1, compositions according to this invention containing paraquat and diuron, and particularly having a much higher ratio of paraquat:diuron than the 2:1 Surefire composition, produced control that was as good as or better than the Surefire composition.

What is claimed is:

1. A soluble liquid herbicidal composition comprising:
   (a) a herbicidally effective amount of a bipyridilium herbicide;
   (b) a photosynthesis-inhibiting phenylurea herbicide;
   (c) a normally water-insoluble oil in which the photosynthesis-inhibiting herbicide (b) is soluble;
   (d) water; and
   (e) a surfactant selected from:
      (i) a polyalkyl glucoside;
      (ii) a polyoxypropylene-polyoxyethylene block copolymer;
      (iii) an alkyl trimethyl ammonium salt; and
      (iv) a mixture of polyvinyl alcohol with a surfactant having an HLB value from about 13 to about 20.

2. A composition according to claim 1 containing:
   from about 5 to about 30 weight % bipyridilium herbicide;
   from about 1 to about 12 weight % photosynthesis-inhibiting herbicide;
   from about 5 to about 20 weight % normally water insoluble oil;
   from about 5 to about 40 weight % surfactant;
   the remainder comprising water.

3. A composition according to claim 1 containing
   from about 18 to about 24 weight % bipyridilium herbicide;
   from about 1 to about 5 weight % photosynthesis-inhibiting herbicide;
   from about 7 to about 10 weight % normally water-insoluble oil;

from about 8 to about 20 weight % surfactant;
the remainder comprising water.

4. A composition according to claim 1 in which the weight ratio of bipyridilium herbicide to photosynthesis-inhibiting herbicide is from about 4:1 to about 25:1.

5. A composition according to claim 4 in which the weigh ratio is from about 8:1 to about 15:1.

6. A composition according to claim in which the water-insoluble oil is a water-insoluble alcohol, an aromatic hydrocarbon, a halohydrocarbon, a ketone, an ester, a nitrogen-containing compound or a phenol.

7. A composition according to claim in which the water-insoluble oil is tetrahydrofurfuryl alcohol, cyclohexanone, or a naphthalene range aromatic solvent.

8. A composition according to claim 1 in which the surfactant is a mixture of polyvinyl alcohol with a surfactant having an HLB value of from about 13 to about 20.

9. A composition according to claim 6 in which the surfactant, having an HLB value of from about 13 to about 20, is an ethoxylated sorbitan ester, an ethoxylated castor oil surfactant, a polyoxyethylene esterate, or an ethoxylated alkylphenol.

10. A composition according to claim in which the bipyridilium herbicide is paraquat.

11. A composition according to claim 1 in which the bipyridilium herbicide is paraquat and the photosynthesis-inhibiting herbicide is diuron.

* * * * *